(12) United States Patent
Lifshitz et al.

(10) Patent No.: US 7,847,275 B2
(45) Date of Patent: Dec. 7, 2010

(54) METHOD AND APPARATUS FOR TELETHERAPY POSITIONING AND VALIDATION

(75) Inventors: Leon Lifshitz, Rishon Le'tzion (IL); Michael Marash, Rishon Le'tzion (IL)

(73) Assignee: PCure Ltd., Or Yehuda (IL)

( * ) Notice: Subject to any disclaimer, the term of this patent is extended or adjusted under 35 U.S.C. 154(b) by 240 days.

(21) Appl. No.: 12/127,391

(22) Filed: May 27, 2008

(65) Prior Publication Data

US 2008/0317216 A1 Dec. 25, 2008

Related U.S. Application Data

(60) Provisional application No. 60/939,923, filed on May 24, 2007, provisional application No. 61/028,519, filed on Feb. 14, 2008.

(51) Int. Cl.
- *A61B 6/04* (2006.01)
- *A61N 5/00* (2006.01)
- *H05H 13/00* (2006.01)

(52) U.S. Cl. ............ 250/505.1; 250/491.1; 250/492.3; 378/65; 378/195; 378/21

(58) Field of Classification Search ............ 250/505.1, 250/491.1, 492.3; 378/65, 195, 21
See application file for complete search history.

(56) References Cited

U.S. PATENT DOCUMENTS

| | | |
|---|---|---|
| 4,618,133 A | 10/1986 | Siczek |
| 4,870,287 A | 9/1989 | Cole et al. |
| 5,013,018 A | 5/1991 | Sicek |
| 5,036,530 A | 7/1991 | DiGiovanna et al. |
| 5,039,867 A | 8/1991 | Nishihara et al. |
| 5,247,556 A | 9/1993 | Eckert et al. |
| 5,250,019 A | 10/1993 | McGinley |
| 5,398,356 A | 3/1995 | Pfleger |
| 5,574,763 A | 11/1996 | Dehner |
| 5,668,371 A | 9/1997 | Deasy et al. |

(Continued)

FOREIGN PATENT DOCUMENTS

DE 4103588 C1 5/1992

(Continued)

OTHER PUBLICATIONS

Kamada, Tadashi et al., "A Horizontal CT System Dedicated to Heavy-Ion Beam Treatment," Radiotherapy & Oncology 50 (1999), pp. 235-237, Elsevier Science Ireland Ltd., Shannon, Ireland.

(Continued)

*Primary Examiner*—Nikita Wells
(74) *Attorney, Agent, or Firm*—Simon Kahn

(57) ABSTRACT

A patient treatment arrangement is provided which includes a fixed beam irradiation source; and a patient positioning apparatus, the patient positioning apparatus comprising: a support member; a patient securing mechanism arranged to secure a patient to the patient support member; and a patient positioner in communication with the patient support member and operative to achieve positioning of the support member equivalent to rotation of the patient support member about a plurality of axes and translation of the patient support member along a plurality of axes, the patient positioner thereby providing substantially unrestricted variable angular access for irradiation of a target tissue of a patient secured to the patient securing mechanism from the fixed beam irradiation source.

35 Claims, 11 Drawing Sheets

U.S. PATENT DOCUMENTS

| | | | |
|---|---|---|---|
| 5,774,915 A | 7/1998 | Scott et al. |
| 5,778,467 A | 7/1998 | Scott et al. |
| 5,784,734 A | 7/1998 | Scott et al. |
| 5,794,286 A | 8/1998 | Scott et al. |
| 5,879,281 A | 3/1999 | Ein-Gal |
| 5,983,424 A | 11/1999 | Naslund |
| 6,094,760 A | 8/2000 | Nonaka et al. |
| 6,295,671 B1 | 10/2001 | Reesby et al. |
| 6,375,355 B1 | 4/2002 | Fortin |
| 6,386,759 B2 | 5/2002 | Noettling |
| 6,400,791 B1 | 6/2002 | Schwarz |
| 6,416,219 B1 | 7/2002 | Pflaum et al. |
| 6,502,261 B1 | 1/2003 | Harwood |
| 6,611,700 B1 | 8/2003 | Vilsmeier et al. |
| 6,730,921 B2 | 5/2004 | Kraft |
| 6,742,929 B2 | 6/2004 | Horbaschek |
| 6,769,806 B2 | 8/2004 | Moyers |
| 6,780,149 B1 | 8/2004 | Schulte |
| 6,785,360 B1 | 8/2004 | Annis |
| 6,802,564 B2 | 10/2004 | Brockway et al. |
| 6,814,694 B1 | 11/2004 | Pedroni |
| 6,828,792 B1 | 12/2004 | Danby et al. |
| 6,865,253 B2 | 3/2005 | Blumhofer et al. |
| 6,865,411 B2 | 3/2005 | Erbel et al. |
| 6,894,300 B2 | 5/2005 | Reimoser et al. |
| 6,986,179 B2 | 1/2006 | Varadharajulu et al. |
| 7,000,271 B2 | 2/2006 | Varadharajulu |
| 7,003,070 B1 | 2/2006 | Chen et al. |
| 7,020,232 B2 | 3/2006 | Rand et al. |
| 7,043,784 B2 | 5/2006 | Plannerer |
| 7,062,007 B2 | 6/2006 | Morita |
| 7,077,569 B1 | 7/2006 | Tybinkowski et al. |
| 7,125,167 B2 | 10/2006 | Alakkat |
| 7,137,160 B2 | 11/2006 | Hand et al. |
| 7,154,991 B2 | 12/2006 | Earnst et al. |
| 7,173,265 B2 | 2/2007 | Miller et al. |
| 7,640,607 B2 * | 1/2010 | Guertin et al. ............... 5/601 |
| 2002/0057758 A1 | 5/2002 | Stark |
| 2002/0095722 A1 | 7/2002 | Korver, II et al. |
| 2002/0120986 A1 | 9/2002 | Erbel et al. |
| 2003/0058993 A1 | 3/2003 | Bohn |
| 2003/0072416 A1 | 4/2003 | Rasche et al. |
| 2003/0078523 A1 | 4/2003 | Burkhardt et al. |
| 2003/0164459 A1 | 9/2003 | Schardt et al. |
| 2004/0013239 A1 | 1/2004 | Gregerson et al. |
| 2004/0042583 A1 | 3/2004 | Wackerle et al. |
| 2004/0102698 A1 | 5/2004 | Vilsmeier et al. |
| 2004/0125920 A1 | 7/2004 | Zaiki |
| 2004/0162457 A1 | 8/2004 | Maggiore et al. |
| 2004/0172758 A1 | 9/2004 | Alakkat |
| 2004/0199072 A1 | 10/2004 | Sprouse et al. |
| 2005/0065675 A1 | 3/2005 | Georgi et al. |
| 2005/0138732 A1 | 6/2005 | Erbel et al. |
| 2005/0222505 A1 | 10/2005 | Damadian et al. |
| 2005/0228255 A1 | 10/2005 | Saracen et al. |
| 2005/0281374 A1 | 12/2005 | Cheng et al. |
| 2006/0002511 A1 | 1/2006 | Miller et al. |
| 2006/0042009 A1 | 3/2006 | Somasundaram et al. |
| 2006/0050848 A1 | 3/2006 | Vilsmeier et al. |
| 2006/0106301 A1 | 5/2006 | Kats |
| 2006/0262898 A1 | 11/2006 | Partain et al. |
| 2007/0003010 A1 * | 1/2007 | Guertin et al. ............... 378/63 |
| 2008/0086816 A1 | 4/2008 | Farooqui |
| 2009/0168960 A1 * | 7/2009 | Jongen et al. ............... 378/65 |

FOREIGN PATENT DOCUMENTS

| | | |
|---|---|---|
| EP | 1121957 A2 | 8/2001 |
| EP | 1380262 A1 | 1/2004 |
| EP | 1384494 A1 | 1/2004 |
| EP | 1288322 A1 | 2/2004 |
| EP | 1388322 A1 | 2/2004 |
| EP | 1454653 A1 | 9/2004 |
| EP | 1867284 A1 | 12/2007 |
| JP | 03-075071 A2 | 3/1991 |
| JP | 08-229145 A2 | 9/1996 |
| JP | 2001-095932 A2 | 4/2001 |
| JP | 2001161839 A | 6/2001 |
| WO | WO 94/10908 A3 | 5/1994 |
| WO | WO 98/18523 A1 | 5/1998 |
| WO | WO 99/53997 A1 | 10/1999 |
| WO | WO 03/059433 A2 | 7/2003 |
| WO | WO 03/070101 A1 | 8/2003 |
| WO | WO 2004/010381 A1 | 1/2004 |
| WO | WO 2005/018734 A2 | 3/2005 |
| WO | WO 2007/012649 A1 | 2/2007 |
| WO | WO 2007/017211 A2 | 2/2007 |
| WO | WO 2007/045076 A1 | 4/2007 |
| WO | WO 2007/062788 A1 | 6/2007 |

OTHER PUBLICATIONS

Kats, M. M., "Planar System Replacing Gantry for Protons and Carbon Ion Beams Transportation," Proceedings of the Sixth European Particle Accelerator Conference (EPAC '98), pp. 2362-2364, Moscow, Russia.

* cited by examiner

METHOD AND APPARATUS FOR TELETHERAPY POSITIONING AND VALIDATION

CROSS-REFERENCE TO RELATED APPLICATIONS

This application claims priority to U.S. Provisional Patent Application Ser. No. 60/939,923 filed May 24, 2007, entitled "Teletherapy Positioning and Validation," and is related to U.S. Provisional Patent Application Ser. No. 61/028,519, entitled "Irradiation Treatment Apparatus and Method," filed on Feb. 14, 2008. This application is also related to U.S. patent application, entitled "Irradiation Treatment Apparatus and Method," filed on even date herewith. Each of the above applications is incorporated herein by reference.

TECHNICAL FIELD

The invention relates generally to the field of teletherapy and, in particular, to a system and method for positioning and validation of a patient before a fixed radiation or particle beam.

BACKGROUND

Teletherapy generally employs an irradiation source disposed at a distance from the body to be treated. X-rays and electron beams have been used in teletherapy to treat various cancers. However, X-rays and electron beams exhibit an energy transfer characteristic approaching an exponential attenuation function and are therefore not optimal for treating deeply embedded growths or target areas. Recently, the use of heavy particles, particularly hadrons, in teletherapy has found increasing acceptance, in part because of the ability of heavy particles to penetrate to a specific depth without appreciably harming intervening tissue. In particular, the energy transfer characteristic of hadrons exhibits an inversed depth profile with a Bragg peak at a location where the hadrons deposit most of their energy, which is approximately at the end of the hadrons' path. As a result of this hadron energy transfer characteristic, increased energy can be directed at or deposited in an embedded growth as compared to X-rays and electron beams. Also, less damage to healthy intervening tissue results when hadron beams are used to treat deep-seated tumors or diseased target tissue.

It should be appreciated that the term "hadrons" can refer to a variety of particles, including protons and other ions that are used in therapy. While this document describes treatment as being accomplished with protons, this is not meant to be limiting in any way and other types of hadrons and ions can be included in such discussion where appropriate.

Typically, in a therapy system, the charged protons or ions are focused into narrow, intensity-modulated, scanned pencil beams of variable penetration depth. In this way, the dose profile can be matched to the target volume. In order to ensure complete irradiation of the target growth, a plurality of beams arriving at the embedded growth from several different directions can be used. The volume in which the plurality of beams intersects, whether the beams are provided sequentially or simultaneously, is often referred to as an isocenter. To improve the biological effectiveness of the treatment, the isocenter is collocated with the target growth to deliver the maximum treatment dose to the target volume and to spare the surrounding tissue.

Present teletherapy systems use a gantry apparatus carrying a beam generating and delivery system. The gantry is a motorized or powered apparatus for moving the massive particle delivery system around a patient who is typically immobilized on a treatment table. Since the beam generating and delivery system is large and extremely heavy, such gantry systems are prohibitively expensive, limiting the number of available proton therapy centers that can provide services to patients. Furthermore, the spatial range of such gantry-driven systems is limited due to mechanical constraints. Movement of the beam generating and delivery system from location to location in order to effect the delivery of the plurality of beams leads to an offset in the isocenter which must be carefully adjusted prior to beam delivery. One example of the above-described treatment systems is illustrated in U.S. Pat. No. 6,769,806 to Moyers.

There is thus a need for an improved teletherapy apparatus that overcomes some or all of the above limitations.

SUMMARY

In view of the discussion provided above and other considerations, the present disclosure provides methods and apparatus to overcome some or all of the disadvantages of prior and present teletherapy systems and methods. Other new and useful advantages of the present methods and apparatus will also be described herein and can be appreciated by those skilled in the art.

Embodiments hereof provide a patient positioning apparatus arranged to enable presentation of a patient at angles and positions relative to a fixed beam irradiation source. In certain embodiments, a wide range of motion in a number of degrees of freedom, including inclinations and rotations of a patient in a patient positioning system are provided. In other embodiments, methods and systems for fixing the patient's body with respect to a patient positioning system and moving the patient positioning system with respect to a fixed beam radiation therapy and/or imaging apparatus are provided. In yet other embodiments, fixed beam radiation therapy apparatus that do not require a gantry for moving the therapy apparatus and where a concurrent spatially-robust imaging and radiation treatment program can be carried out on a patient in a substantially upright (vertically oriented) position are described. Furthermore, the patient in a substantially upright position can be moved with respect to the imaging and therapy apparatus by suitable powered and controlled movement of the patient positioning system within which the patient is secured.

In one or more embodiments, the target tissue volume which is to be treated is delineated from adjacent non-target tissue. A planned target volume (PTV) is determined and a plurality of beam angles, is determined. In some embodiments, for each of the plurality of angles, a preferred distance of the delineated target tissue from the irradiation source is determined. In other embodiments, a predetermined nominal distance is used, with energy levels of the irradiation beam adjusted in place of distance adjustment. In accordance with an aspect hereof the pre-treatment planning comprises positioning the patient at each of the selected beam angles in relation to a fixed beam of the treatment.

Those skilled in the art will appreciate the practical design, engineering, economic, clinical, and other benefits of such a method and apparatus. These benefits include, but are not limited to accurately maintaining a target treatment volume in the proper position with respect to one or more fixed proton beams, improving control over the position and restricting movement of internal organs in or near the target treatment volume. In addition, more efficient treatment of target treatment volumes results in increased capacity and throughput of clinical facilities. Improved targeting of treatment volumes can be accomplished through the present method and apparatus as a result of improved integration of the imaging, treatment planning, and therapeutic portions of a teletherapy procedure.

Additional features and advantages of the invention will become apparent from the following drawings and detailed description.

BRIEF DESCRIPTION OF THE DRAWINGS

For a better understanding of the invention and to show how the same may be carried into effect, reference will now be made, purely by way of example, to the accompanying drawings in which numerals designate corresponding elements or sections throughout.

In the accompanying drawings.

DETAILED DESCRIPTION

Figure 1:
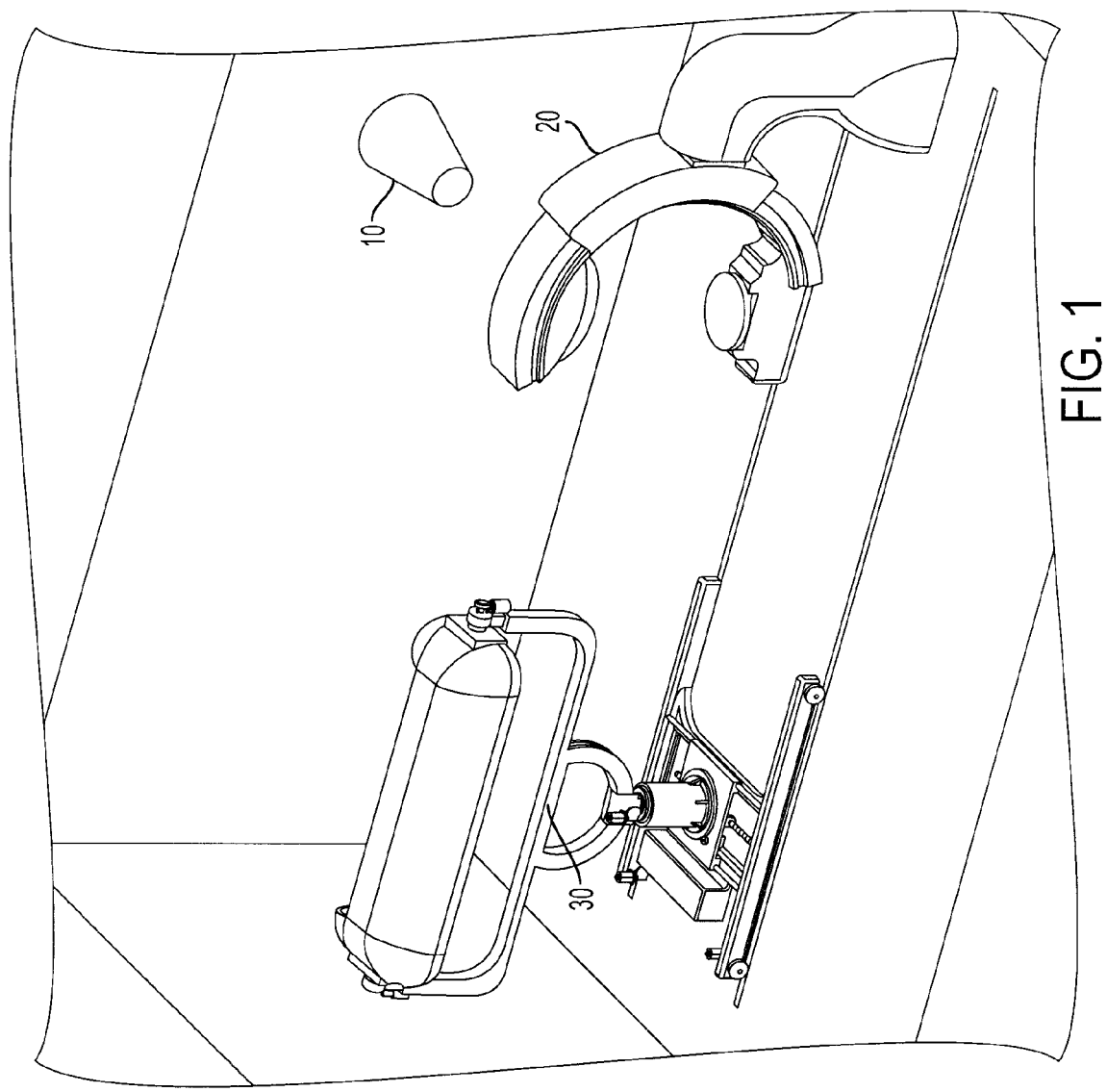
FIG. 1 illustrates an exemplary embodiment of a patient treatment arrangement.

At a pre-treatment planning stage, a patient is secured to a platform, for example, as provided in various embodiments herein or their equivalent. The patient is preferably secured to the platform in a reproducible manner and imaged utilizing one of magnetic resonance imaging, ultrasound imaging, computerized tomography (CT) imaging, x-ray imaging, positron emission tomography imaging and single photon emission computed tomography imaging, or a combination thereof or any other suitable imaging modality that is appropriate for this application.

It is to be understood that the patient is preferably a live human, but can also be an animal, other suitable organs, or target for application of the present teletherapy thereto.

It is also to be understood that fixed beam irradiation may include scanning and scattering technologies, which are sourced from a fixed location charged hadron source with post beam generation scanning or scattering functionality. In addition, fixed beam irradiation is not limited to that from a single fixed beam irradiation source, but can include multiple fixed beams which are independently controlled or jointly controlled.

In order to accomplish teletherapy in accordance with an embodiment hereof a fixed beam irradiation source is supplied in a treatment room. In one embodiment, the fixed beam irradiation source is arranged to controllably output a generally horizontal beam and in another embodiment, the fixed beam irradiation source is arranged to controllably output a generally vertical beam. The fixed beam irradiation source may further exhibit post scanning or scattering functionality without exceeding the scope of the invention. As mentioned above, a plurality of distinct or component fixed beams may be employed to generate the desired effect at the planned target volume.

The patient is placed on the patient support member of a patient positioning apparatus, preferably in a reproducible manner and preferably substantially similar or identical to the placement of the patient achieved in pre-treatment planning. In one embodiment, the patient is placed on the patient support member in a horizontal position. The patient is then fixed to the patient support member by a patient securing mechanism, thereby immobilizing the patient. The patient securing mechanism may comprise, but is not limited to, a harness, straps, a translucent cover, a registration and mobilization mechanism, or a combination thereof.

The patient positioning apparatus is then translated along one or more translational degrees of freedom or axes. For example, the translation may be accomplished along three orthogonal dimensions. However, any practical coordinate system can be used for translating and positioning the patient positioning apparatus, including a Cartesian coordinate system, but the present discussion is not so limited. The patient support platform may be linearly positioned using any suitable drive and control mechanism and the position of the platform may be monitored, accelerated, or stopped using any braking, limiting, or control apparatus practical for a given application and design.

In addition, the patient support platform may be rotated about one or more rotational degrees of freedom. In some embodiments, the rotational degrees of freedom provide rotation substantially about the translational axes. For example, rotation about three orthogonal axes may be used to present the delineated target tissue in the planned target volume to the fixed radiation or particle beam at a determined beam angle and optionally associated distance in accordance with a pre-treatment planning procedure.

The translation along the one or more translational degrees of freedom, and the rotation about one or more rotational degrees of freedom can be carried out by separately translating and then rotating the platform, or can be carried out by translating and rotating the platform at the same time, or in increments or combinations thereof. In some embodiments, a plurality of translations and rotations are provided which result in patient positioning equivalent to translation along of each of three orthogonal dimensions and rotation about each of three orthogonal axes.

As part of imaging or irradiating the patient in the teletherapy process, a plurality of treatment beam angles or paths into the patient's body can be used. The platform can be positioned to accommodate one beam angle or path at a time, moving between a first and second irradiation beam or path instance. Alternatively, the platform can be positioned to allow multiple beams or beam paths to coincide to treat the patient as needed or as determined in a pretreatment planning procedure.

Prior to irradiation at a first of a plurality of beam angles, imaging of the target tissue is accomplished and the patient positioning apparatus is adjusted as required by translating and/or rotating the platform as described above so as to achieve a desired patient position with respect to the imaging and/or treatment beams. The movement of the patient positioning platform can be equivalent to translation along each of three orthogonal dimensions and rotation about three orthogonal axes as required, to finely correct the presentation of the delineated target tissue in the planned target volume to the fixed radiation or particle beam at the first of the plurality of beam angles and optional associated distance therefrom.

The imaging of the target tissue is preferably accomplished using one or more of an ultrasound imager, a CT imager, a magnet resonance imager, an x-ray imager, a fluoroscope, a positron emission tomography (PET) imager, an optical camera (operating in a visible or infrared range of the spectrum) and a single photon emission computed tomography (SPECT) imager.

In one particular embodiment, a C-arm CT imager is utilized. A C-arm CT imager provides computed tomographic images of a region of interest using source-detector pairs arranged along a substantially C-shaped arm which can be moved about the region of interest. Irradiation of the target tissue at the first of the plurality of beam angles from the fixed beam irradiation source is then performed on a planned target volume within the imaged region of interest.

Following treatment at the first beam angle or path the patient positioning platform is translated and/or rotated so as to achieve a second position as needed to continue the treatment at a second beam angle or path. For example, the patient is positioned equivalent to translation along each of three orthogonal dimensions and rotation about three orthogonal axes as required to present the delineated target tissue to the fixed radiation or particle beam at a second of the plurality of beam angles and optional associated distance, in accordance with the pre-treatment planning. There is no requirement that the translation and rotation to a second of the plurality of beam angles be accomplished at the same treatment session as the translation and rotation to the first beam angle. The use of multiple treatment sessions, in which the patient may no longer be secured to the platform between individual treatment sessions, may be used.

Prior to irradiation at the second of the plurality of beam angles, imaging of the target tissue is preferably again accomplished. If needed, the patient presentation is adjusted again by the translating and/or rotating the patient positioning platform so as to achieve a desired positioning equivalent to translation along each of three orthogonal dimensions and rotation about three orthogonal axes. Note that movement of the platform and patient is not limited to movement along orthogonal axes. The patient positioning platform can thereby automatically or manually be driven to finely correct the presentation of the delineated target tissue to the fixed radiation or particle beam at the second of the plurality of beam angles and optional associated distance. Irradiation of the target tissue at the second of the plurality of beam angles is then performed.

It is to be understood that in the event that irradiation at the first and second beam angles is accomplished at a single treatment session, i.e. the patient remains secured to the patient positioning apparatus and there is no change in the relevant organ positions due to gravity, imaging of the target tissue at the second beam angle is not required. In one non-limiting illustrative example, in the event that the first and second beam angles result in the patient being in an upright position and only differ in a rotation about a vertical axis defined by the patient body vertical axis, no second imaging is required.

The above is repeated as required for additional angles and treatments thereby providing teletherapy utilizing hadrons such as protons without expensive gantries to move the radiation source apparatus about the patient or treatment center. It should be noted that having a fixed beam radiation system can provide advantages for shielding or other considerations because the direction and incidence of the fixed beam is predictable and stationary.

The present embodiments enable presentation of a patient at any angle and position relative to a fixed beam irradiation source and/or an imaging apparatus.

At a pre-treatment planning stage, the patient is secured to a platform preferably identical to the platform of the subject invention and preferably in a reproducible manner and imaged utilizing one of magnetic resonance imaging, ultrasound imaging, computerized tomography (CT) imaging, x-ray imaging, positron emission tomography imaging and single photon emission computed tomography imaging, or a combination thereof. The target tissue is delineated from adjacent non-target tissue; a planned target volume is determined; and the plurality of beam angles, and optionally the associated preferred distance of the delineated target tissue from the irradiation source for each of the plurality of angles, are determined. Alternatively, or in combination therewith, the energy of the irradiation beam is adjusted as a substitute for distance adjustment. In accordance with an aspect of the invention in one embodiment the pre-treatment planning comprises positioning the patient at each of the selected beam angles in relation to a fixed beam of the ultimate treatment.

It is to be understood that the term fixed beam irradiation source, as used in this document, does not exclude scanning and scattering technologies, which are sourced from a fixed location charged hadron source with post beam generation scanning or scattering functionality. It is also to be understood that the term fixed beam irradiation source, as used in this document, is not limited to a single fixed beam irradiation source, and multiple fixed beams, which are independently controlled or joint controlled, may be supplied without exceeding the scope of the invention.

In order to accomplish teletherapy in accordance with an embodiment of the subject invention, a fixed beam irradiation source is supplied in a treatment room. In one embodiment, the fixed beam irradiation source is arranged to controllably output a generally horizontal beam, in another embodiment, the fixed beam irradiation source is arranged to controllably output a generally vertical beam, and in yet another embodiment, a horizontal and/or a generally vertical beam are provided in combination with an angled beam. The fixed beam irradiation source may further exhibit post scanning or scattering functionality without exceeding the scope of the invention.

The patient is placed on the patient support member of a patient positioning apparatus of the subject invention, preferably in a reproducible manner and preferably substantially identical to the placement of the pre-treatment planning. In one embodiment, the patient is placed on the patient support member in a horizontal position. The patient is then fixed to the patient support member by a patient securing mechanism, thereby immobilizing the patient. The platform is then translated and rotated so as to achieve a desired positioning equivalent to translation along each of three orthogonal dimensions and rotation about three orthogonal axes as required, to present the delineated target tissue to the fixed radiation or particle beam at a first of the plurality of beam angles and optional associated distance in accordance with the pre-treatment planning.

Prior to irradiation at the first of the plurality of beam angles, imaging of the target tissue is again accomplished, and the patient presentation is adjusted as required by the platform being translated and rotated so as to achieve a desired positioning equivalent to translation along each of three orthogonal dimensions and rotation about three orthogonal axes as required to finely correct the presentation of the delineated target tissue to the fixed radiation or particle beam at the first of the plurality of beam angles and optional associated distance. The imaging of the target tissue is preferably by one or more of an ultrasound imager, a CT imager, a magnet resonance imager, an x-ray imager, a fluoroscope, a positron emission tomography imager and a single photon emission computed tomography imager. In one particular embodiment, a C-arm CT imager is utilized. Irradiation of the target tissue at the first of the plurality of beam angles from the fixed beam irradiation source is then performed.

The platform is then translated and rotated so as to achieve a desired positioning equivalent to translation along each of three orthogonal dimensions and rotation about three orthogonal axes as required to present the delineated target tissue to the fixed radiation or particle beam at a second of the plurality of beam angles and optional associated distance in accordance with the pre-treatment planning. There is no requirement that the translation and rotation to a second of the plurality of beam angles be accomplished at the same treatment session as the translation and rotation to the first beam angle, and the use of multiple treatment sessions, in which the patient may no longer be secured to the platform between individual treatment sessions, may be used.

Prior to irradiation at the second of the plurality of beam angles, imaging of the target tissue is preferably again accomplished and the patient presentation is adjusted as required by the platform being translated and rotated so as to achieve a desired positioning equivalent to translation along each of three orthogonal dimensions and rotation about three orthogonal axes as required to finely correct the presentation of the delineated target tissue to the fixed radiation or particle beam at the second of the plurality of beam angles and optional associated distance. Irradiation of the target tissue at the second of the plurality of beam angles is then performed. It is to be understood that in the event that irradiation at the first and second beam angles is accomplished at a single treatment session, i.e. the patient remains secured to the patient positioning apparatus, and there is no change in the relevant organ positions due to gravity, imaging of the target tissue at the second beam angle is not required. In one non-limiting illustrative example, in the event that the first and second beam angles result in the patient being in an upright position, and only differ in a rotation about a vertical axis defined by the patient body vertical axis, no second imaging is required.

The above is repeated as required for additional angles and treatments thereby providing teletherapy utilizing hadrons such as protons without expensive gantries.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1 illustrates a high level perspective drawing of a patient treatment arrangement in accordance with a principle of the current invention, comprising a fixed beam irradiation source 10, an imager 20, and a patient positioning apparatus 30. Imager 20 is illustrated as a C-arm CT imager, however this is not meant to be limiting in any way. In another embodiment, imager 20 is selected from among an ultrasound imager, a CT imager, a magnet resonance imager, an x-ray imager, a fluoroscope, a positron emission tomography imager and a single photon emission computed tomography imager, and may comprise a combination of imagers without exceeding the scope of the invention.

Fixed beam irradiation source 10 is arranged to output a generally horizontal radiation beam, however, this is not meant to be limiting in any way. Alternative fixed beam irradiation source arrangements may also be used. In another embodiment, fixed beam irradiation source 10 is arranged to output a generally vertical radiation or particle beam, entering from one of the top and the bottom of the treatment room, without exceeding the scope of the invention. In yet another embodiment, fixed beam irradiation source 10 is arranged to output a radiation or particle beam at a fixed angle relative to a base plane of the patient positioning apparatus 30 without exceeding the scope of the invention. A combination of a plurality of fixed beam irradiation sources 10 may be provided without exceeding the scope of the invention.

Figure 2:
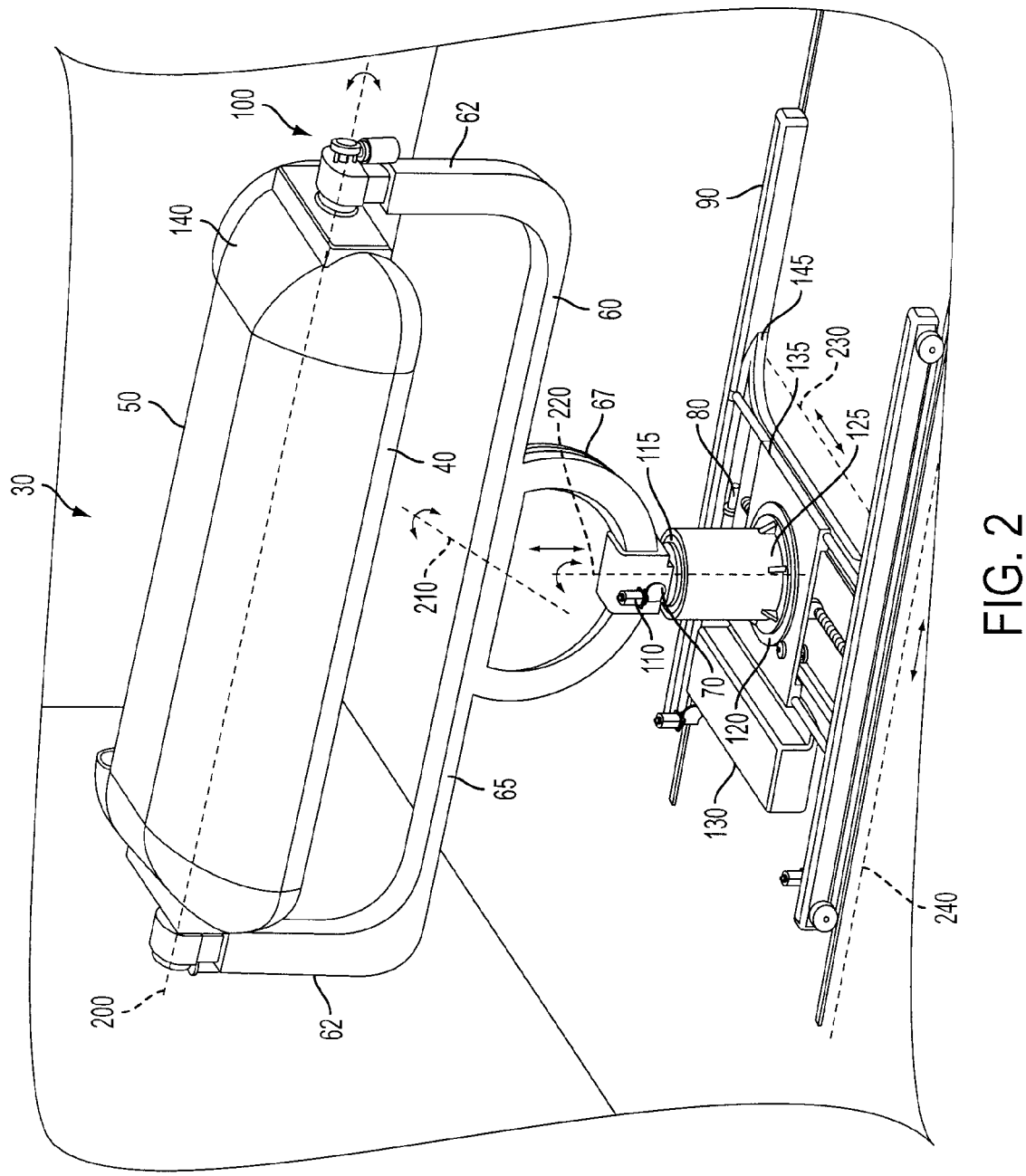
FIG. 2 illustrates an exemplary embodiment of a patient positioning apparatus.

FIG. 2 illustrates a high level perspective drawing of a first embodiment of a patient positioning apparatus 30 in accordance with a principle of the subject invention, comprising: a patient support member 40, a patient securing mechanism 50, a support fork 60, a first translation mechanism 70, a second translation mechanism 80, a third translation mechanism 90, a first rotation mechanism 100, a second rotation mechanism 110, a third rotation mechanism 120, a control mechanism 130, and an optional fiducial marker 140. The combination of a first translation mechanism 70, second translation mechanism 80, third translation mechanism 90, first rotation mechanism 100, second rotation mechanism 110, and third rotation mechanism 120 comprises a positioning mechanism or positioner operative to translate and rotate patient support member 40.

A single fiducial marker is shown for ease of understanding, however it is to be understood that there is no limitation to the number of fiducial markers which may be provided in accordance with a principle of the invention. In one embodiment, a fiducial marker 140 is provided on the patient, and in another embodiment, a fiducial marker 140 is provided on the patient support member 40. Alternatively, fiducial marker 140 may be absent without exceeding the scope of the invention. Each of first translation mechanism 70, second translation mechanism 80 and third translation mechanism 90 are arranged to translate patient support member 40 along a respective orthogonal axis as will be described further. Each of first rotation mechanism 100, second rotation mechanism 110, and third rotation mechanism 120 are arranged to rotate patient support member 40 about a respective orthogonal axis as will be described further.

Support fork 60, exhibiting a pair of arms 62 and a base 65, secures patient support member 40, while allowing for rotation of patient support member 40 about a first rotation axis 200. Rotation of patient support member 40 about first rotation axis 200 is controlled by first rotation mechanism 100, described further below, arranged to rotatably connect respective arms 62 to opposing longitudinal ends of patient support member 40. In one embodiment, first rotation mechanism 100 provides controlled rotation of patient support member 40 about first rotation axis 200 of up to 180°, in another embodiment up to 270° and in yet another embodiment up to 360°. In one embodiment, the first rotation axis 200 is coincident with a center line axis of patient support member 40, proceeding in a generally longitudinal manner.

Base 65 of support fork 60 is connected to arm 67 which is retained by second rotation mechanism 110. Rotation of patient support member 40 about a second rotation axis 210, which is orthogonal to first rotation axis 200, is controlled by second rotation mechanism 110, as will be described further hereinto below. Arm 67 is illustrated as being semicircular, thus limiting the rotation about axis 210 to 180°, however this is not meant to be limiting in any way. In an alternative embodiment (not shown), arm 67 is about three quarters circular and is connected to base 65 at the open ends thereof, thus providing rotation about axis 210 of up to 270°. In yet another embodiment (not shown), arm 67 is circular and is tangentially connected to base 65, thus providing rotation around axis 210 of up to 360°.

Second rotation mechanism 110 is connected to one end of an axially slidable piston 115 and the variably unexposed portion of axially slideable piston 115 is surrounded by a cylinder 125. Axially slideable piston 115 is raised or lowered along a first translation and third rotation axis 220 by a hydraulic mechanism as will be described further hereinto below.

Cylinder 125 is rotatably connected to a table 135, the rotation of cylinder 125 about first translation and third rotation axis 220 being controlled by third rotation mechanism 120, described further hereinto below. Rotation about first translation and third rotation axis 220 is orthogonal to axes 200, 210 described above. In one embodiment, third rotation mechanism 120 provides controlled rotation of patient support member 40 about third rotation axis 220 of up to 180°, in another embodiment up to 270° and in yet another embodiment up to 360°.

Table 135 is translatable along a second translation axis 230, orthogonal to first translation and third rotation axis 220, by second translation mechanism 80. Table 135 is supported by carriage 145, which is translatable along a third translation axis 240, orthogonal to each of first translation and third rotation axis 220 and second translation axis 230 described above, by third translation mechanism 90.

In operation, patient positioning apparatus 30 is placed in a neutral loading position, preferably presenting patient support member 40 horizontally and unobstructedly to enable ease of entry. A patient is placed in a supine position upon patient support member 40 and secured in place by patient securing mechanism 50. Patient securing mechanism 50 is illustrated as a cover translucent to the beam output by fixed beam irradiation source 10 and to the operative imaging mechanism of imager 20, however this is not meant to be limiting in any way. Preferably, patient securing mechanism 50 comprises a mechanism for registration and immobilization. In another embodiment, patient securing mechanism 50 may comprise one or more of: a registration and mobilization mechanism, a registration and mobilization mechanism, and a registration and mobilization mechanism.

Once the patient is secured and immobilized in relation to patient support member 40 by patient securing mechanism 50, patient support member 40 is translated and rotated to be within the imaging zone of imager 20. The translation and rotation of patient support member 40 is controlled by control mechanism 130 which is operative to control each of first 70, second 80, and third 90 translation mechanisms and first 100, second 110, and third 120 rotation mechanisms. Advantageously, patient support member 40 with a patient secured thereon is thus rotatable about any of three orthogonal axes and translatable along any of three orthogonal axes. In one embodiment, patient support member 40 is rotatable 180° about each of three orthogonal axes, in another embodiment patient support member 40 is rotatable up to 270° about at least two of three orthogonal axes and in yet another embodiment patient support member 40 is rotatable up to 360° about at least two of three orthogonal axes.

In a pre-treatment session, imager 20 is utilized to delineate the target tissue of the patient, and pre-treatment planning methodology known to those skilled in the art is used to determine a treatment plan for the identified target tissues, the treatment plan typically comprising a plurality of different irradiation angles and optional associated distances of the delineated target tissue from the irradiation source for each of the plurality of angles. Alternatively, the distances and/or the energy level of the fixed beam irradiation source may be adjusted accordingly. Advantageously, patient support member 40, with a patient secured thereon, may be translated and rotated as required to present the target tissue at best presentation angle and position for capture by imager 20. Optionally, fiducial marker 140 is used in cooperation with visual positioning systems known to those skilled in the art to ensure proper initial positioning of patient positioning apparatus 30. Optional fiducial marker 140 is illustrated as being exhibited by patient securing means 50, however this is not meant to be limiting in any way.

In another embodiment, optional fiducial marker 140 is placed on the patient or embedded therein, without exceeding the scope of the invention. In one non-limiting embodiment an implantable transducer is used to aid in the repeated identification of the target tissue and thus fiducial marker 140 comprises the implanted transducer. In one non-limiting embodiment, fiducial marker 140 comprises an x-ray visible marker.

In a first treatment session, patient support member 40, with the patient secured thereon by patient securing mechanism 50, is translated along any or all three translation axes 220, 230, 240 and rotated about any or all three rotation axes 200, 210, 220 as required under control of control mechanism 130, to present the identified target tissue in line with a radiation or particle beam controllable exiting fixed beam irradiation source 10 in accordance with a first irradiation angle of the plurality of radiation angles of the determined treatment plan and the optional associated distance of the delineated target tissue from fixed beam irradiation source 10.

It is to be understood that in the event that a fixed distance is utilized and energy levels are adjusted, in one embodiment, a nominal distance is set. Preferably, imager 20 is further operative under control of control mechanism 130, or a separate imaging control mechanism (not shown) to image the translated and rotated patient at the first irradiation angle. Responsive to the imaging by imager 20, patient positioning apparatus 30 may be finely translated along any of three orthogonal translation axes 220, 230, 240 and rotated about any of three orthogonal rotation axes 200, 210, 220 to ensure accurate beam positioning, in terms of angle and optional distance, from fixed beam irradiation source 10. Optionally, after any fine translation and rotation, the patient may be again imaged by imager 20 as required.

If required, due to the mechanical constraints of imager 20, imager 20 is then rotated or translated out of the line of the radiation or particle beam controllably emanating from fixed beam irradiation source 10 to the patient secured on patient support member 40. The patient is then irradiated from fixed beam irradiation source 10 at the first irradiation angle of the plurality of radiation angles of the determined treatment plan.

In the event of a single angle treatment per treatment session, patient positioning apparatus 30 is then translated along any or all of three translation axes 220, 230, 240 and rotated about any or all of three rotation axes 200, 210, 220 as required under control of control mechanism 130, to place patient positioning apparatus 30 in the neutral loading position, preferably presenting patient support member 40 horizontally and unobstructedly to enable ease of exit.

In a second treatment session, patient support member 40, with the patient secured thereon by patient securing mechanism 50, is translated along any or all of three translation axes 220, 230, 240 and rotated about any or all of three rotation axes 200, 210, 220 as required under control of control mechanism 130, to present the identified target tissue in line with fixed beam irradiation source 10 in accordance with a second irradiation angle of the plurality of radiation angles of the determined treatment plan and the optional associated distance of the delineated target tissue from fixed beam irradiation source 10.

In another embodiment, imager 20 is further operative under control of control mechanism 130, or a separate imaging control mechanism (not shown) to image the translated and rotated patient at the second irradiation angle. Responsive to the imaging by imager 20, patient positioning apparatus 30 may be finely translated along any of three orthogonal translation axes 220, 230, 240 and rotated about any of three orthogonal rotation axes 200, 210, 220 to ensure accurate beam positioning, in terms of angle and optional distance, from fixed beam irradiation source 10. Optionally, after any fine translation and rotation, the patient may be again imaged by imager 20 as required.

If required, due to the mechanical constraints of imager 20, imager 20 is then rotated or translated out of the line of the radiation or particle beam controllably emanating from fixed beam irradiation source 10 to the patient secured on patient support member 40. The patient is then irradiated from fixed beam irradiation source 10 at the second irradiation angle of the plurality of radiation angles of the determined treatment plan.

Additional treatment angles, and optional associated distances are accomplished as described above, and may be accomplished at a single multiple treatment session or at separate treatment sessions without exceeding the scope of the invention.

Figure 3A:
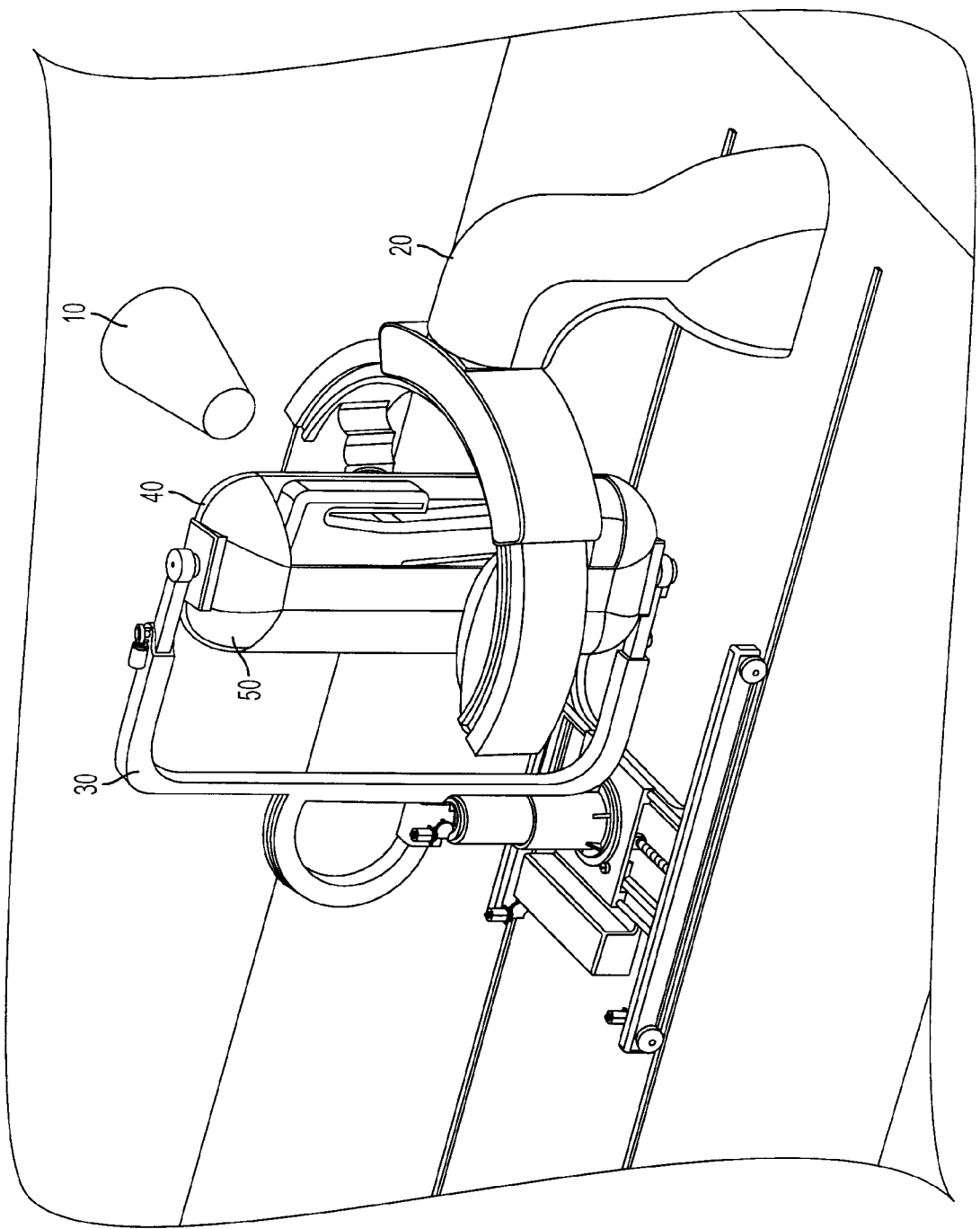
FIG. 3A illustrates an exemplary embodiment of a patient treatment arrangement where the imager is rotated for imaging, in which the patient secured on the patient support member at one of the plurality of treatment angles in line with a beam exiting a fixed beam irradiation source.

The above has been described in relation to patient positioning apparatus 30 being independently translatable along each of three orthogonal dimensions and about each of three orthogonal axes, however this is not meant to be limiting in any way. In another embodiment (not shown), patient positioning apparatus 30 is arranged to be translatable and rotatable along a combination of dimensions and axes so as to achieve a desired positioning equivalent to translation along each of three orthogonal dimensions and about three orthogonal axes as required FIG. 3A illustrates a high level perspective drawing of the patient treatment arrangement of FIG. 1, in accordance with a principle of the current invention, in which imager 20, illustrated as a C-arm CT, is rotated for imaging the patient secured on patient support member 40 by patient securing mechanism 50 at one of the plurality of treatment angles in line with a radiation or particle beam exiting fixed beam irradiation source 10. It is to be noted that by virtue of first 70, second 80, and third 90 translation mechanisms and first 100, second 110 and third 120 rotation mechanisms of FIG. 2, patient support member 40 has been translated along first 220, second 230, and third 240 translation axes and has been rotated about first 200, second 210 and third 220 rotation axes from the neutral position of FIG. 2. In particular, in the non-limiting example shown, patient support member 40 has been rotated from a horizontal position to a vertical position, and further rotated to face fixed beam irradiation source 10. Imager 20 is illustrated as a C-arm CT imager, however this is not meant to be limiting in any way. In another embodiment, imager 20 is selected from among an ultrasound imager, a CT imager, a magnet resonance imager, an x-ray imager, a fluoroscope, a positron emission tomography imager, a single photon emission computed tomography imager, or may comprise a combination of imagers without exceeding the scope of the invention.

Fixed beam irradiation source 10 is shown arranged to output a generally horizontal radiation or particle beam, however this is not meant to be limiting in any way. In another embodiment, fixed beam irradiation source 10 is arranged to output a generally vertical beam, entering from the top and the bottom of the treatment room without exceeding the scope of the invention. In yet another embodiment, fixed beam irradiation source 10 is arranged to output a beam at a fixed angle relative to a base plane of patient positioning apparatus 30 without exceeding the scope of the invention.

Figure 3B:
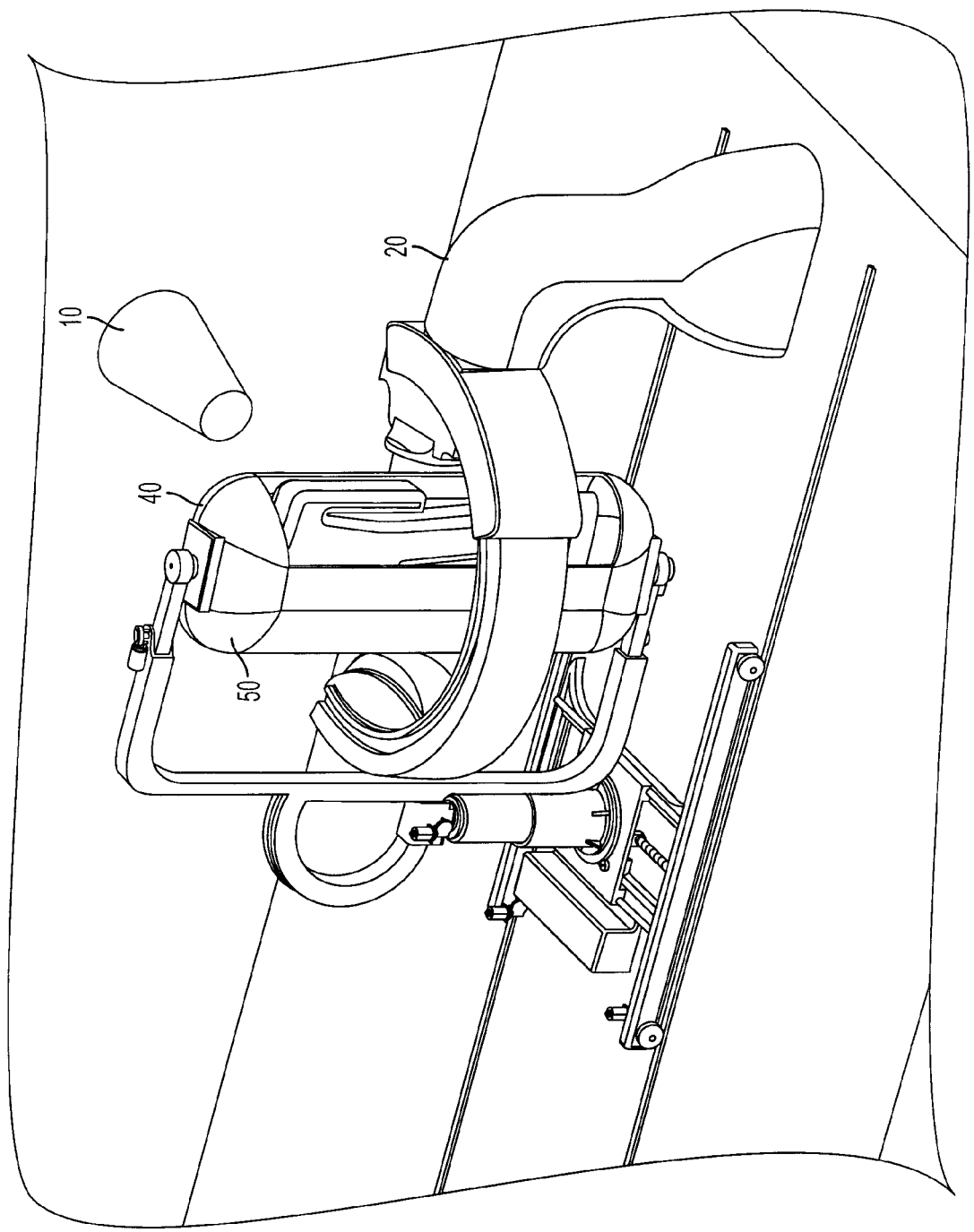
FIG. 3B illustrates an exemplary embodiment of a patient treatment arrangement where the imager is rotated so as not to obstruct a beam exiting a fixed beam irradiation source.

FIG. 3B illustrates a high level perspective drawing of the patient treatment arrangement of FIG. 1, in accordance with a principle of the current invention, in which imager 20, illustrated as a C-arm CT, is rotated, preferably after imaging the patient secured on patient support member 40 by patient securing mechanism 50, so as not to obstruct a particle beam exiting fixed beam irradiation source 10. Imager 20 is illustrated as a C-arm CT imager, however this is not meant to be limiting in any way. In another embodiment imager 20 is selected from among an ultrasound imager, a CT imager, a magnet resonance imager, an x-ray imager, a fluoroscope, a positron emission tomography imager and a single photon emission computed tomography imager, and may comprise a combination of imagers without exceeding the scope of the invention.

Figure 4B:
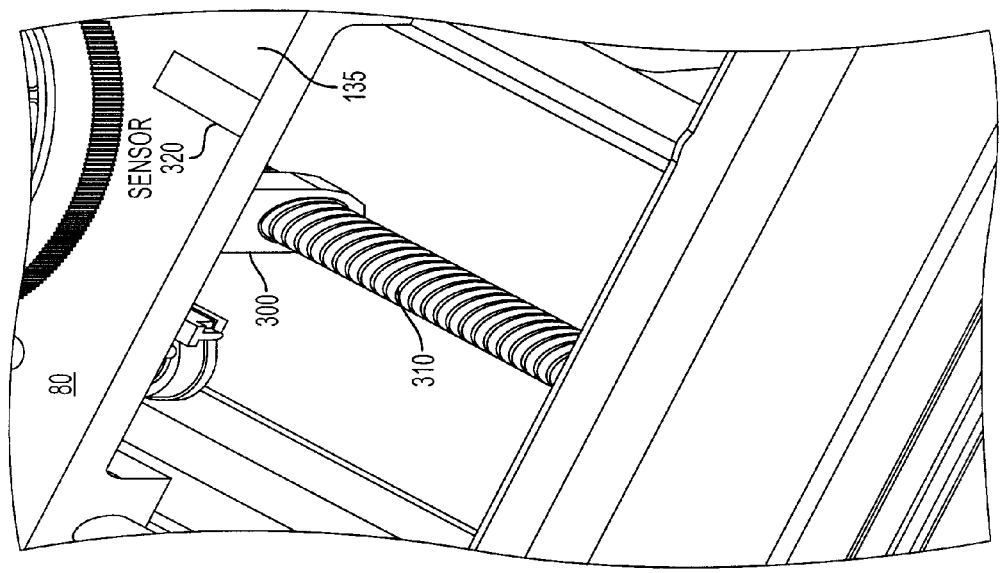
FIG. 4B illustrates an exemplary embodiment of a second translation mechanism of a patient positioning apparatus.
Figure 4A:
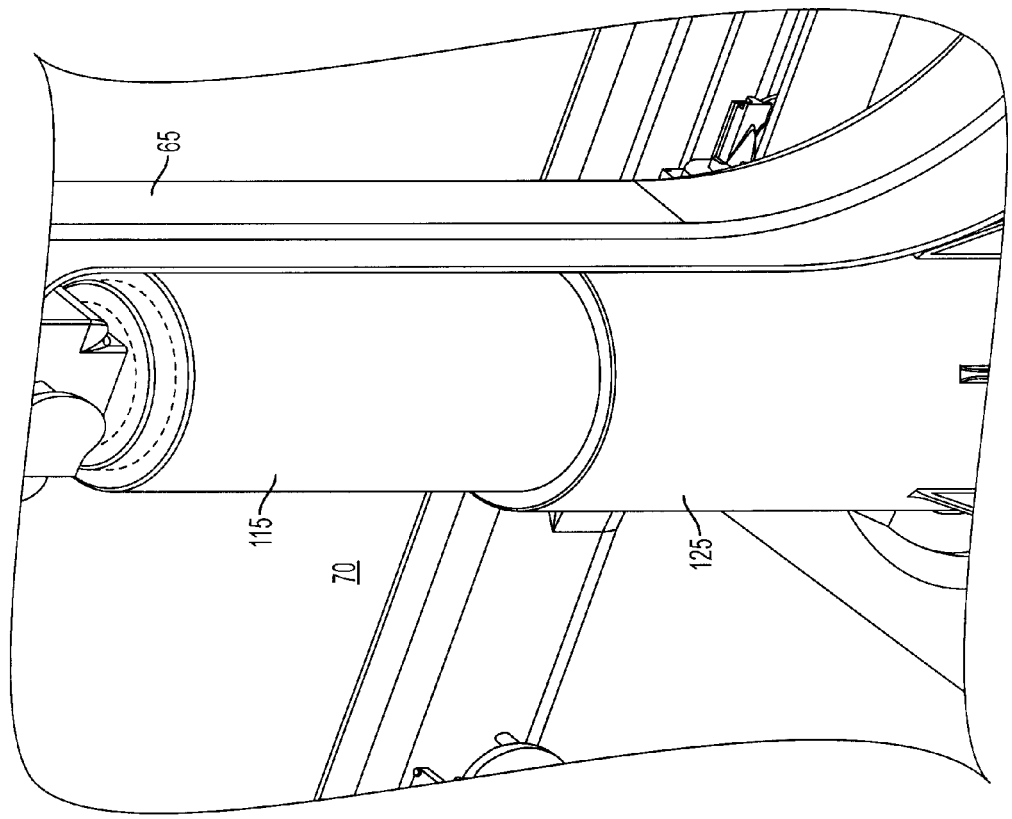
FIG. 4A illustrates an exemplary embodiment of a first translation mechanism of a patient positioning apparatus.

FIG. 4A illustrates a detailed picture of first translation mechanism 70, exhibiting axially slidable piston 115 contactingly surrounded by cylinder 125 in accordance with a principle of the invention. Axially slideable piston 115 is raised or lowered along first translation axis 220 by a hydraulic mechanism under control of control mechanism 130 of FIG. 2. Preferably, the extension of slidable piston 115 is confirmed to control mechanism 130 by an external sensor (not shown) comprising one or more of a mechanical sensor, a piezoelectric sensor, an inductive sensor, an optical sensor, or a capacitive sensor. Base 65 of support fork 60 is shown in a vertical position, reflecting rotation of patient support member 40 about second rotation axis 210 to the vertical position.

FIG. 4B illustrates a detailed picture of second translation mechanism 80, exhibiting table 135 to which is secured a threaded receiver 300, further exhibiting a turnable shaft 310 in accordance with a principle of the invention. Turnable shaft 310 is rotatable by a worm gear assembly and stepper motor (not shown) controllable by control mechanism 130 of FIG. 2. Preferably, the location of table 135 is confirmed to control mechanism 130 by an external sensor 320 comprising one or more of a mechanical sensor, a piezoelectric sensor, an inductive sensor, an optical sensor, or a capacitive sensor.

Figure 4C:
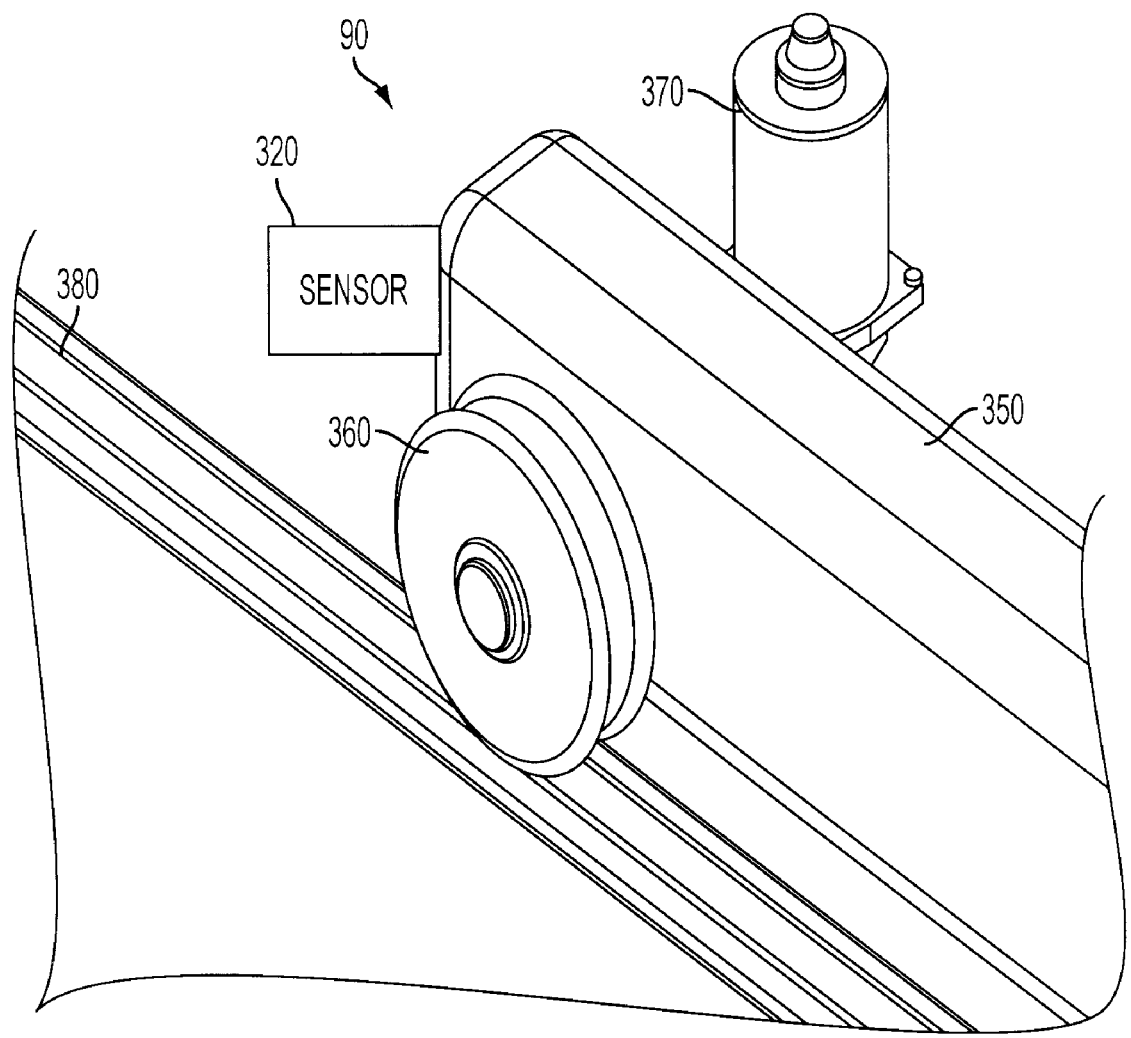
FIG. 4C illustrates an exemplary embodiment of a third translation mechanism of a patient positioning apparatus.

FIG. 4C illustrates a detailed picture of third translation mechanism 90, comprising outrider arm 350 to which is secured a controlled wheel 360 operative by a worm gear (not shown) rotated by a stepper motor 370 controllable by control mechanism 130 of FIG. 2 in accordance with a principle of the invention. Preferably, wheel 360 is retained within a track 380 thereby limiting motion of outrider arm 350 to be along third translation axis 240 of FIG. 2. The precise location of wheel 360 is confirmed to control mechanism 130 by external sensor 320 comprising one or more of a mechanical sensor, a piezoelectric sensor, an inductive sensor, an optical sensor, or a capacitive sensor.

Figure 5A:
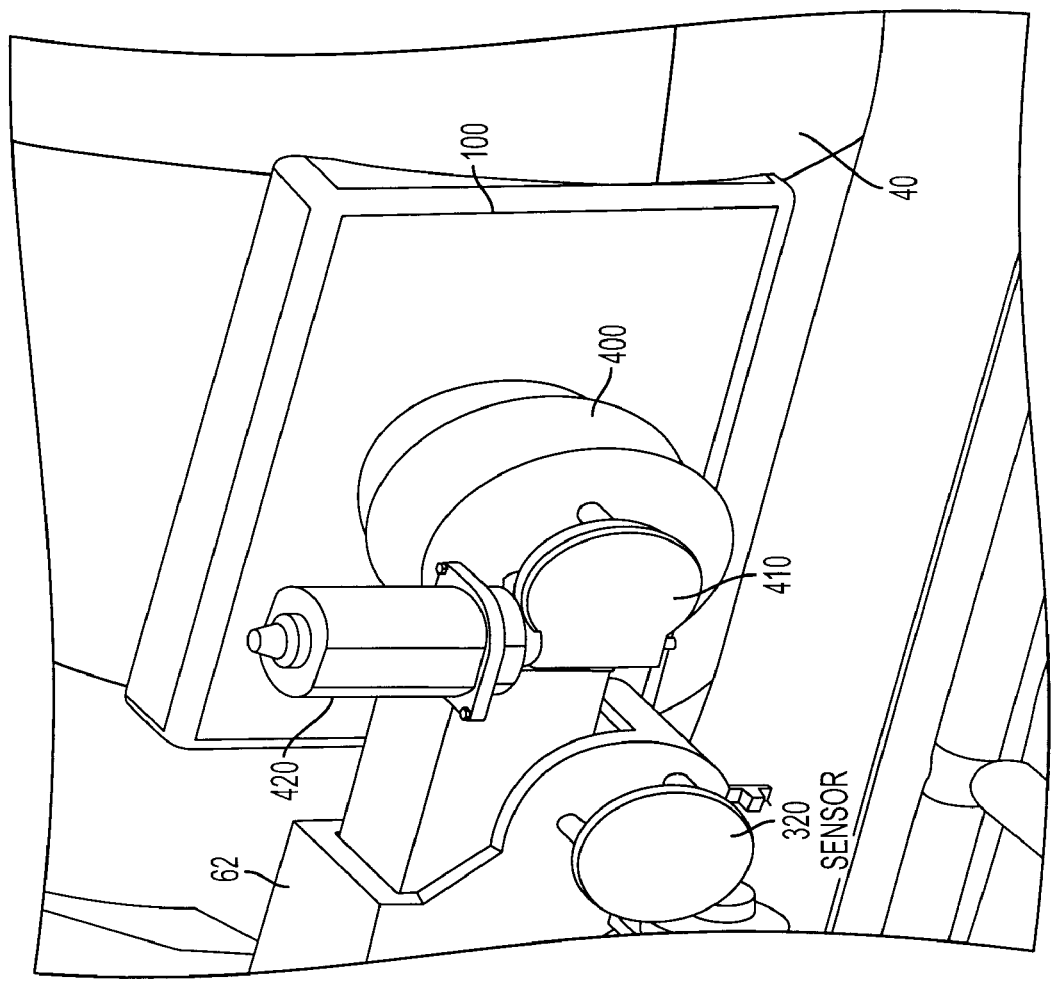
FIG. 5A illustrates an exemplary embodiment of a first rotation mechanism of a patient positioning apparatus.

FIG. 5A illustrates a detailed picture of first rotation mechanism 100, comprising an end of one arm 62 of support fork 60 of FIG. 2 rotatably connected at rotation joint 400 to patient support member 40 in accordance with a principle of the invention. Patient support member 40 is controllably rotated by a stepper motor 420 engaging a worm gear 410. Stepper motor 420 is controlled by control mechanism 130 of FIG. 2. The precise rotation of patient support member 40 is confirmed to control mechanism 130 by external sensor 320 comprising one or more of a mechanical sensor, a piezoelectric sensor, an inductive sensor, an optical sensor, or a capacitive sensor.

Figure 5C:
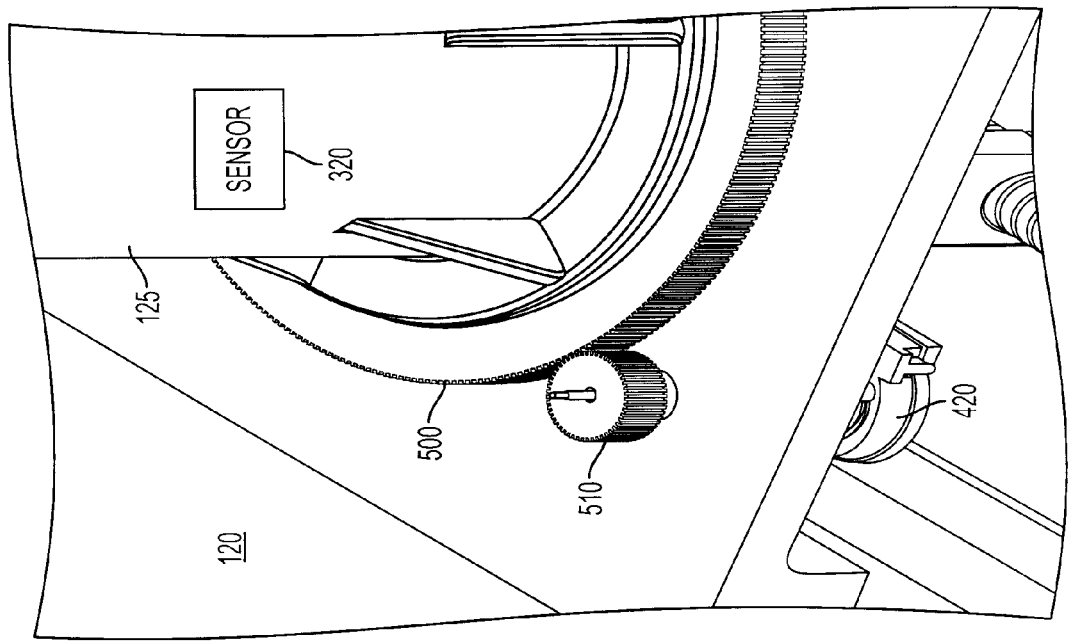
FIG. 5C illustrates an exemplary embodiment of a third rotation mechanism of a patient positioning apparatus.
Figure 5B:
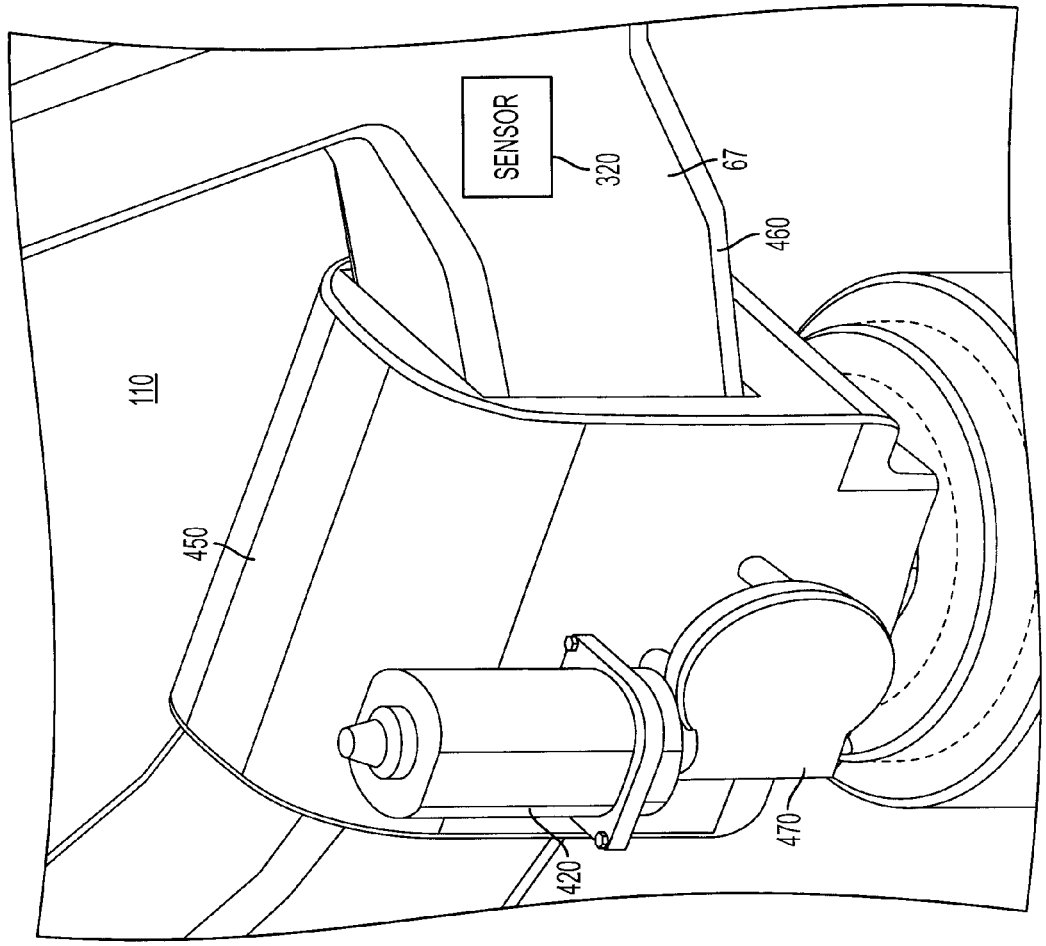
FIG. 5B illustrates an exemplary embodiment of a second rotation mechanism of a patient positioning apparatus.

FIG. 5B illustrates a detailed picture of second rotation mechanism 110, comprising arm 67 secured within holder 450 in accordance with a principle of the invention. Arm 67 further exhibits teeth 460 on an underside thereof engaging matching teeth of gear 470. Gear 470 is rotated by the action of stepper motor 420 in a worm gear arrangement and stepper motor 420 is controlled by control mechanism 130 of FIG. 2. The precise rotation of arm 67 is confirmed to control mechanism 130 by external sensor 320 comprising one or more of a mechanical sensor, a piezoelectric sensor, an inductive sensor, an optical sensor and a capacitive sensor.

FIG. 5C illustrates a detailed picture of third rotation mechanism 120, comprising cylinder 125 exhibiting an external toothed ring 500 secured at one end thereof, in accordance with a principle of the invention. External toothed ring 500 is arranged to engage toothed capstan 510 which is controllably rotated by stepper motor 420 controlled by control mechanism 130 of FIG. 2. The precise rotation of cylinder 125 is confirmed to control mechanism 130 by external sensor 320 comprising one or more of a mechanical sensor, a piezoelectric sensor, an inductive sensor, an optical sensor, or a capacitive sensor.

Figure 6:
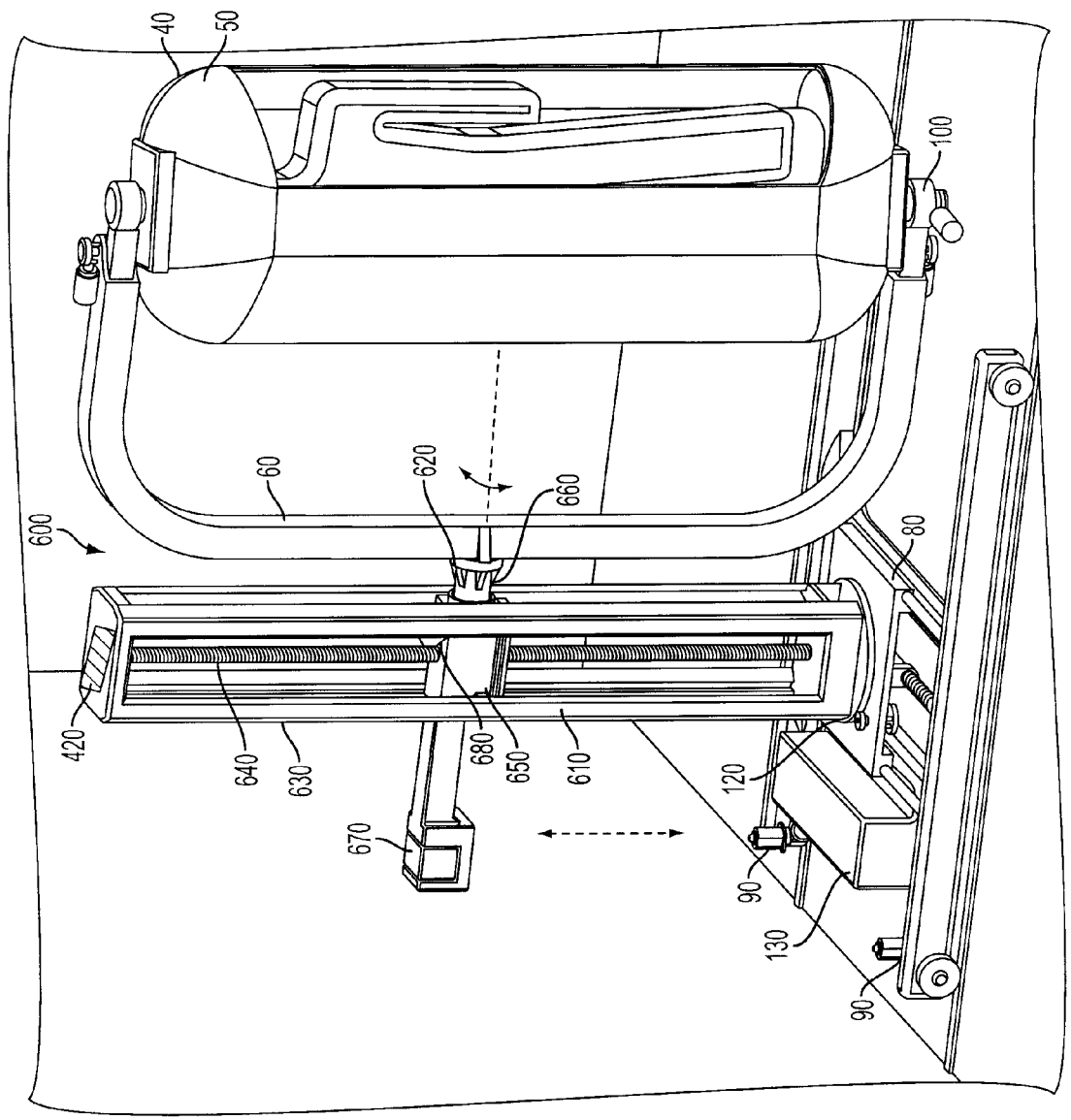
FIG. 6 illustrates an exemplary embodiments of a patient positioning apparatus.

FIG. 6 illustrates a high level perspective drawing of another embodiment of a patient positioning apparatus, denoted patient positioning apparatus 600, in accordance with a principle of the subject invention, comprising: a patient support member 40, a patient securing mechanism 50, a support fork 60, a first translation mechanism 610, a second translation mechanism 80, a pair of third translation mechanisms 90, a first rotation mechanism 100, a second rotation mechanism 620, a third rotation mechanism 120, and a control mechanism 130. Each of first translation mechanism 610, second translation mechanism 80 and third translation mechanisms 90 are arranged to translate patient support member 40 along a respective orthogonal axis as described above in relation to FIG. 2. The combination of a first translation mechanism 610, second translation mechanism 80, third translation mechanisms 90, first rotation mechanism 100, second rotation mechanism 620, and third rotation mechanism 120 comprises a positioning mechanism or positioner operative to translate and rotate patient support member 40. Each of first rotation mechanism 100, second rotation mechanism 620 and third rotation mechanism 120 are arranged to rotate patient support member 40 about a respective orthogonal axis as described above in relation to FIG. 2.

The operation of patient positioning apparatus 600 is in all respects similar to that of patient positioning apparatus 30 of FIG. 2 with the exception of first translation mechanism 610 and second rotation mechanism 620 which will now be further explained. First translation mechanism 610 comprises a tower 630 and an extended worm gear 640 traversing the length thereof. Worm gear 640 is arranged to cooperate with a threaded support assembly 650 and to be rotated by stepper motor 420 under control of control mechanism 130. Optionally, a sensor (not shown) is provided to enable closed loop position feedback to control mechanism 130.

Second rotation mechanism 620 comprises a rotating arm 660 securing fork 60 and counterbalanced by a counterweight 670. The rotation of rotating arm 660 is under control of a stepper motor 680 engaging teeth of rotating arm 660 in a worm gear arrangement. Stepper motor 680 is under control of control mechanism 130. Optionally, a sensor is provided to enable closed loop position feedback to control mechanism 130.

The above has been described in relation to patient positioning apparatus 600 being independently translatable along each of three orthogonal dimensions and about each of three orthogonal axes, however this is not meant to be limiting in any way. In another embodiment (not shown), patient positioning apparatus 600 is arranged to be translatable and rotatable along a combination of dimensions and axes so as to achieve a desired positioning equivalent to translation along each of three orthogonal dimensions and about three orthogonal axes as required In another embodiment (not shown), a robot such as a Fanuc model M-900iA, available from Fanuc, Ltd. of Japan and exhibiting 6 articulated axes, is connected to support, translate, and rotate a patient support member 40 so as to achieve a desired positioning equivalent to translation along each of three orthogonal dimensions and about three orthogonal axes in accordance with a principle of the invention. The selection of the appropriate robot must take into account the loaded weight of patient support member 40 and patient securing mechanism 50. However, use of such a robot may incur additional expense and dimensions in excess of the described embodiments.

Figure 7:
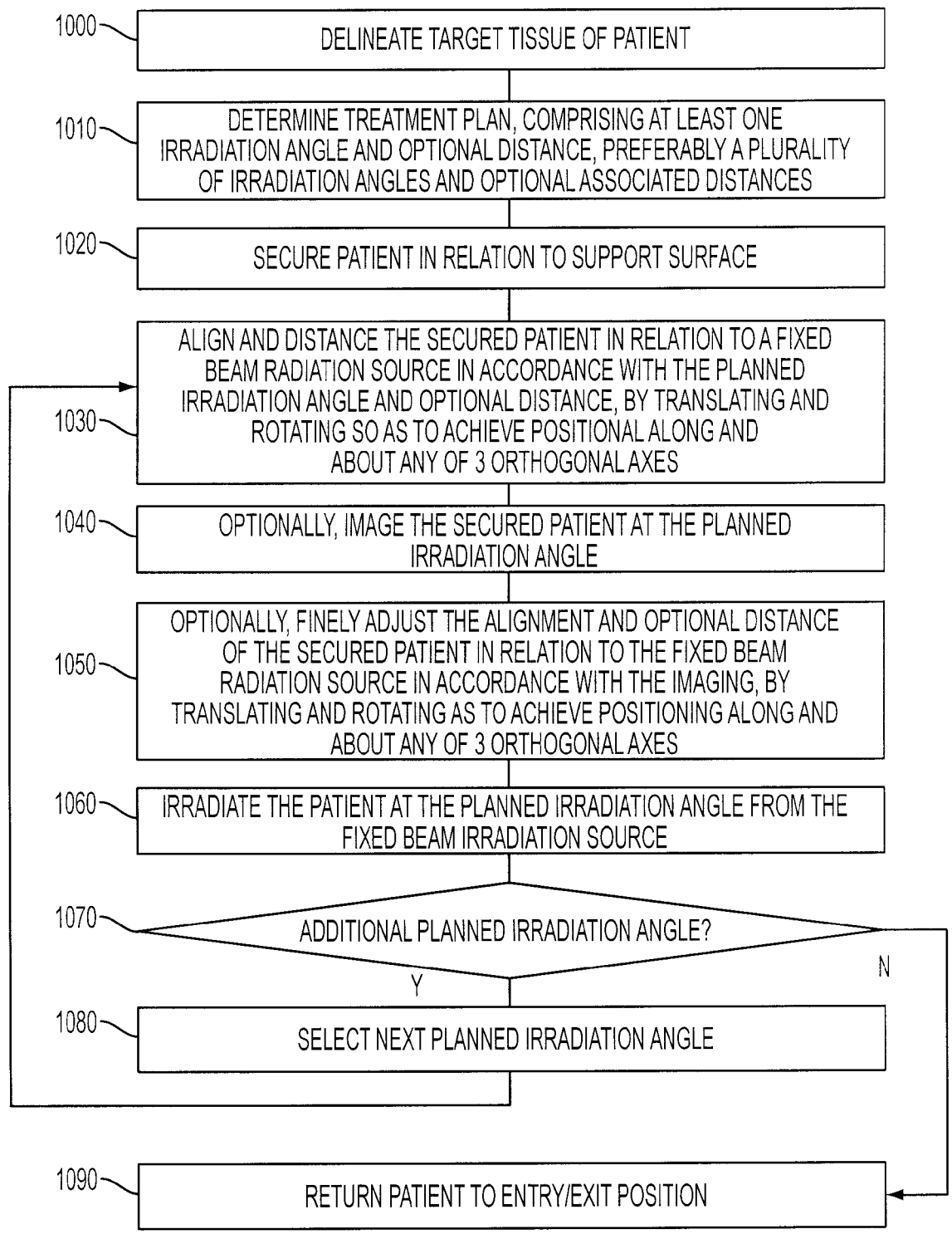
FIG. 7 illustrates an exemplary flow chart of a method for irradiating a target tissue volume at a planned irradiation angle from a fixed beam irradiation source.

FIG. 7 illustrates a high level flow chart of a method according to a principle of the invention to irradiate a target tissue at a planned irradiation angle to a fixed beam irradiation source, and an optional associated distance there from. In stage 1000, a target tissue is delineated. In one embodiment, the target tissue is delineated by securing the patient in relation to a fixed support member, such as patient support member 40 in cooperation with patient securing mechanism 50. In one non-limiting embodiment, the target tissue is delineated by rotating and translating the patient secured to a positioning apparatus in accordance with a principle to the invention to an appropriate angle and presentation in relation to a fixed imager, such as one or more of a C-arm CT imager, an ultrasound imager, a CT imager, a magnet resonance imager, an x-ray imager, a fluoroscope, a positron emission tomography imager, or a single photon emission computed tomography imager. There is no requirement that stage 1000 be accomplished in cooperation with patient positioning apparatus 30, 600. In one embodiment, patient support member 40, in cooperation with or without patient securing means 50, is used in the delineation of stage 1000, such as with an axial CT imager.

In stage 1010, a treatment plan comprising at least one angle of irradiation and optionally, an associated distance from fixed radiation or particle beam, preferably comprising a plurality of irradiation angles and optional associated distances, is determined.

In stage 1020, a patient is secured in relation to a fixed support member, such as patient support member 40 in cooperation with patient securing mechanism 50. Preferably, stage 1020 is performed with patient positioning apparatus 30 set at a neutral, unencumbered horizontal entry/exit position. Alternatively, a vertical neutral unencumbered horizontal entry/exit position is provided without exceeding the scope of the invention.

In stage 1030, the secured patient of stage 1020 is aligned and distanced in relation to a fixed beam irradiation source in accordance with an angle and optional distance of the treatment plan of stage 1010. The patient is aligned and distanced by translating and rotating so as to achieve a desired positioning equivalent to translation along each of three orthogonal dimensions and about three orthogonal axes as required. In one embodiment, the rotating is up to 180° about each of the three orthogonal axes. In another embodiment, the rotating is up to 270° about at least two of the three orthogonal axes and in yet another embodiment, the rotating is up to 360° about at least two of the three orthogonal axes. In an embodiment in which distances are not determined for each treatment angle, the distancing is, in one embodiment, in accordance with a nominal distance.

In optional stage 1040, the patient secured to the patient support member of stage 1020 is imaged at the angle of the treatment plan of stage 1010. The imaging is preferably by one or more of an ultrasound imager, a computerized tomography imager, a magnet resonance imager, an x-ray imager, a fluoroscope, a positron emission tomography imager or a single photon emission computed tomography imager. In one particular embodiment a C-arm CT imager is utilized. Imaging the patient at the irradiation angle advantageously enables for compensation for organ movement due to angle of presentation.

In optional stage 1050, responsive to the optional imaging of stage 1040, the alignment and optional distance of the patient secured to the patient support member of stage 1020 is finely adjusted in relation to the fixed beam irradiation source in accordance with the angle and optional distance of the treatment plan of stage 1010. The fine adjustment comprising translating and rotating the patient support member achieves a desired positioning equivalent to translation along each of three orthogonal dimensions and about three orthogonal axes as required.

In stage 1060, the patient is irradiated from a fixed beam irradiation source at the planned irradiation angle. Preferably the fixed beam irradiation source comprises hadrons, further preferably protons.

In stage 1070, the treatment plan of stage 1010 is consulted. In the event an additional planned irradiation angle is contemplated, in stage 1080 the next planned irradiation angle and optional associated distance is selected and stage 1030 as described above is performed for next planned irradiation angle and associated distance. It is to be understood that in the event that irradiation at a plurality of beam angles is accomplished at a single treatment session and there is no change in the relevant organ positions due to gravity, imaging of the target tissue at the second beam angle of stage 1040 is not required. In one non-limiting illustrative example, in the event that the first and second beam angles result in the patient being in an upright position and only differ in a rotation about a vertical axis defined by the patient body vertical axis, no second imaging of stage 1040 is required There is no requirement that stage 1030 be performed directly after stage 1060, and in one embodiment, the patient is released as will be described further in relation to stage 1090, with stage 1030 being performed again at a future treatment session. In such an embodiment, stage 1020 is performed prior to stage 1030 at the future treatment session, without requiring stages 1000 and 1010.

In the event that in stage 1070 an additional planned irradiation angle is not contemplated, in stage 1090 the patient secured to the patient support member of stage 1020 is rotated and translated to return to the neutral entry/exit position described above in relation to stage 1020. The patient is then disengaged from patient securing mechanism 50 and patient support member 40.

Figure 8:
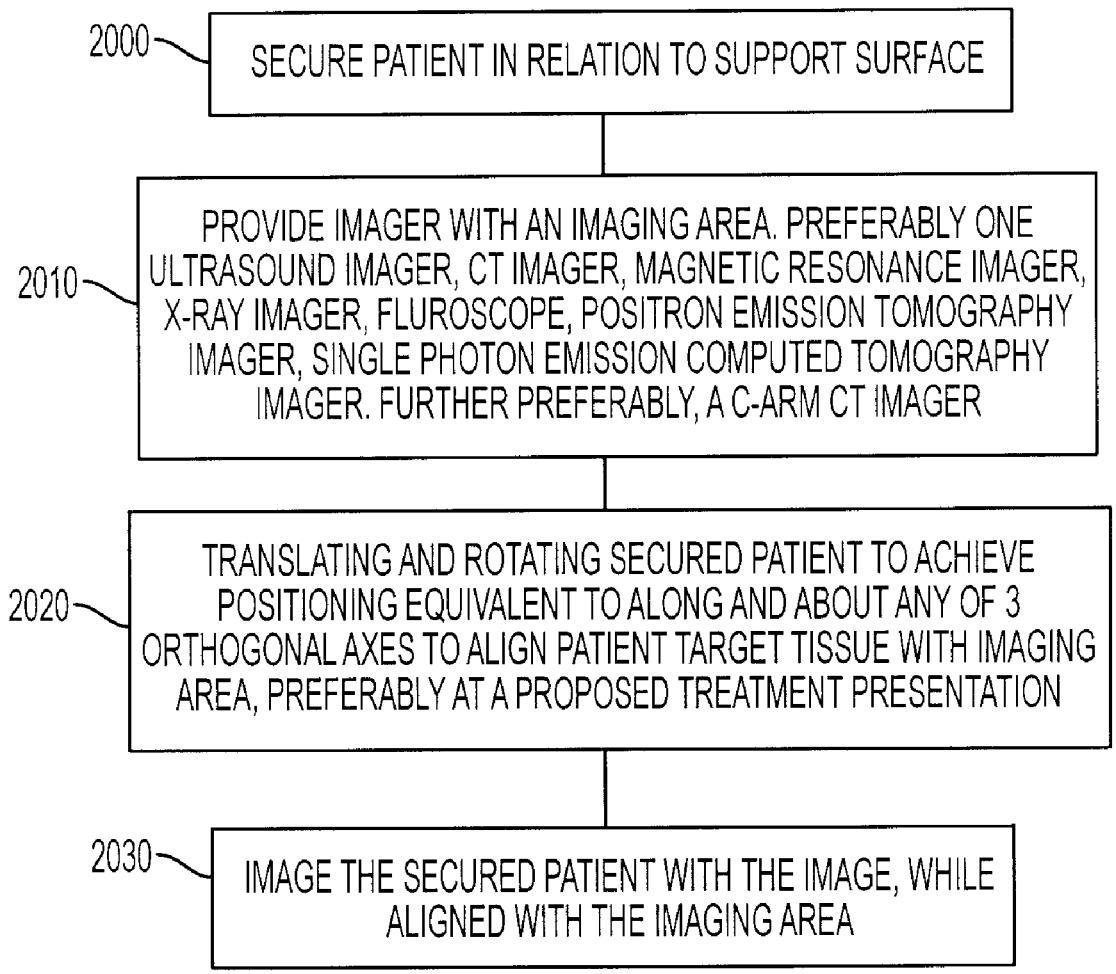
FIG. 8 illustrates another exemplary flow chart of a method according to an embodiment hereof.

FIG. 8 illustrates a high level flow chart of a method according to a principle of the invention to determine a treatment plan in cooperation with patient positioning apparatus 30, 600 of FIGS. 2, 6. Preferably, a proposed treatment presentation has been developed, and the method of FIG. 8 enables imaging of a patient target tissue with a patient secured in the proposed treatment presentation.

In stage 2000, a patient is secured in relation to a fixed support member, such as patient support member 40 in cooperation with patient securing mechanism 50. Preferably, stage 2000 is performed with patient positioning apparatus 30 set at a neutral unencumbered horizontal entry/exit position. Alternatively, a vertical neutral unencumbered horizontal entry/exit position is provided without exceeding the scope of the invention.

In stage 2010, an imager is provided exhibiting an imaging area, such as imager 20 of FIGS. 1, 3A, 3B. In one embodiment, the provided imager is a C-arm CT. In another embodiment, the imager is one or more of an ultrasound imager, a CT imager, a magnetic resonance imager, an x-ray imager, a fluoroscope, a positron emission tomography imager, or a single photon emission computed tomography imager.

In stage 2020, the secured patient of stage 2000 is translated and rotated so as to achieve a desired positioning equivalent to translation along each of three orthogonal dimensions and about three orthogonal axes as required to align the patient target tissue with the imaging area of the imager of stage 2010 at the proposed treatment presentation. The patient is aligned and optionally distanced by translating and rotating the patient support member equivalent to translation and rotation along and about 3 orthogonal axes. In one embodiment, the rotating is up to 180° about each of the three orthogonal axes. In another embodiment, the rotating is up to 270° about at least two of the three orthogonal axes and in yet another embodiment, the rotating is up to 360° about at least two of the three orthogonal axes.

In stage 2030, the secured patient of stage 2000, aligned with imager as a result of stage 2020, is imaged with the imager of stage 2010. Thus, a patient may be imaged at any presentation angle, allowing for improved visualization of target tissues and/or obstructions.

Thus, the present embodiments enable presentation of a patient at any angle and position relative to a fixed beam irradiation source and/or an imaging apparatus.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The terms "include", "comprise" and "have" and their conjugates as used herein mean "including but not necessarily limited to".

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

We claim:

1. A patient positioning apparatus comprising:
a patient support member;
a positioner coupled to the patient support member, the positioner adapted to translate the patient support member along any of three orthogonal axes and rotate the patient support member at least 180° about each of the three orthogonal axes so as to position the patient support member with respect to a fixed treatment beam; and
a patient securing mechanism coupled to the patient support member, the patient securing mechanism arranged to secure a patient to the patient support member and immobilize the patient over the entire range of translation and rotation of the positioner.

2. The patient positioning apparatus of claim 1, wherein the positioner is adapted to rotate the patient support member at least 270° about at least two of the three orthogonal axes.

3. The patient positioning apparatus of claim 1, further adapted to position the patient support member with respect to an imager, wherein the imager consists of at least one of ultrasound, computerized tomography, magnetic resonance imaging, fluoroscopy, positron emission tomography, or single photon emission computed tomography.

4. The patient positioning apparatus of claim 1, wherein the patient support member is substantially vertical while the patient is treated.

5. The patient positioning apparatus of claim 1, wherein the positioner comprises of at least one translation mechanism and at least one rotation mechanism.

6. The patient positioning apparatus of claim 1, wherein the translation mechanism is adapted to translate the patient support member and the rotation mechanism is adapted to rotate the patient support member.

7. The patient positioning apparatus of claim 5, further comprising a control system in communication with the rotation mechanism and the translation mechanism, the rotation mechanism and the translation mechanism being responsive to the control system.

8. The patient positioning apparatus of claim 7, further comprising at least one fiducial marker, the control system in communication with an visual positioning system arranged to detect the at least one fiducial marker.

9. The patient positioning apparatus of claim 1, wherein at least a portion of the patient securing mechanism consists of a radiolucent material.

10. The patient positioning apparatus of claim 1, wherein the patient securing mechanism is operative to secure the patient to the patient support member to restrict patient movement while rotating the patient support member.

11. A method of positioning a patient support member with respect to a fixed beam irradiation source comprising:
securing and immobilizing a patient in relation to a patient support member, the patient support member adapted to translate the patient support member along any of three orthogonal axes and rotate the patient support member at least 180° about each of the three orthogonal axes, the securing and immobilizing being over the entire range of the translation and rotation of the patient support member;
aligning the patient in relation to the fixed beam irradiation source in accordance with a first irradiation angle;
imaging a target tissue of the patient while in the first irradiation angle;
adjusting the alignment of the patient responsive to the imaging in accordance with the first irradiation angle;
irradiating the target tissue of the patient from the fixed beam irradiation source at the first irradiation angle;
aligning the patient in relation to the fixed beam irradiation source in accordance with a second irradiation angle; and
irradiating the target tissue of the secured patient from the fixed beam radiation at the second irradiation angle.

12. The method of claim 11, wherein the patient support member is adapted to rotate the patient support member at least 270° about at least two of the three orthogonal axes.

13. The method of claim 11, wherein imaging of the target tissue of the secured patient aligned with the first irradiation angle is performed by one of ultrasound, computerized tomography, magnet resonance imaging, x-ray imaging, fluoroscopy, positron emission tomography and single photon emission computed tomography.

14. The method of claim 11, wherein imaging of the target tissue of the secured patient aligned with the first irradiation angle is performed by a C-arm computerized tomography imager.

15. The method of claim 11, further comprising after aligning the secured patient in accordance with the second irradiation angle and prior to irradiating the secured patient at the second irradiation angle:
imaging the secured patient aligned in accordance with the second irradiation angle; and
adjusting the alignment of the secured patient responsive to imaging of the secured patient aligned in accordance with the second irradiation angle.

16. The method of claim 15, wherein the imaging of the target tissue of the secured patient aligned with the second irradiation angle is performed by one of ultrasound, computerized tomography, magnetic resonance imaging, x-ray imaging, fluoroscopy, positron emission tomography and single photon emission computed tomography.

17. The method of claim 11, wherein the patient support member is adapted to rotate the patient support member up to 360° about at least two of the three orthogonal axes.

18. The method of claim 11, wherein the fixed beam irradiation source comprises a proton source.

19. The method of claim 11, wherein the fixed beam irradiation source comprises a hadron source.

20. The method of claim 11, wherein irradiating the target tissue of the secured patient from the fixed beam irradiation source at the first irradiation angle is at a different treatment session than irradiating the target tissue of the secured patient from the fixed beam radiation at the second irradiation angle.

21. The method of claim 11, wherein the treatment plan further comprises for each of the first and second irradiation angles an associated distance from the fixed beam irradiation source, and wherein aligning the secured patient in relation to the provided fixed beam irradiation source in accordance with the first irradiation angle further comprises distancing the secured patient in accordance with the associated distance and wherein aligning the secured patient in relation to the provided fixed beam irradiation source in accordance with the second irradiation angle further comprises distancing the secured patient in accordance with the associated distance.

22. A patient positioning apparatus, comprising:
a fixed beam irradiation source; and
a patient positioning member including a support member, a patient positioner in communication with the patient support member and operative to achieve positioning of the support member equivalent to rotation of the patient support member of at least 180° about any one of three orthogonal axes and translation of the patient support member along any of three orthogonal axes, and a patient securing mechanism arranged to secure and immobilize a patient to the patient support member over the entire range of rotation and translation of the patient positioner,
the patient positioner thereby providing unrestricted variable angular access positioning for irradiation of a target tissue of a patient secured to the patient securing mechanism from the fixed beam irradiation source.

23. The patient positioning apparatus of claim 22, further comprising:
a control system,
the patient positioner in communication with the control system and operative responsive to the control system.

24. The patient positioning apparatus of claim 23, further comprising at least one fiducial marker, and wherein the patient treatment arrangement further comprises:
a position detection system operative in cooperation with the at least one fiducial marker and in communication with the control system,
the control system being operative responsive to the position detection system to control the unrestricted variable angular access.

25. The patient positioning apparatus of claim 23, wherein the positioner further comprises one of a mechanical position identifier, a piezoelectric position identifier, an inductive position identifier, a capacitive sensor and an optical sensor in communication with the control system.

26. The patient positioning apparatus of claim 22, wherein the patient positioner is operative to achieve the positioning of the support member equivalent to rotation of the patient support member of at least 270° about at least two of the three orthogonal axes.

27. A patient treatment arrangement according to claim 22, wherein the patient positioner is operative to achieve the positioning of the support member equivalent to rotation of the patient support member of 360° about at least two of the three orthogonal axes.

28. A patient treatment arrangement according to claim 22, wherein at least a portion of the patient securing mechanism is constituted of a radiolucent material.

29. A patient treatment arrangement according claim 22, wherein the patient securing mechanism secures the patient to the patient support member without allowing for patient movement throughout the rotation of the patient support member.

30. A patient treatment arrangement according to claim 22, further comprising an imager operative to provide an image of the target in the any of the unrestricted variable angular access positions.

31. A patient treatment arrangement according to claim 30, wherein the imager comprises a C-arm computerized tomography imager.

32. A patient treatment arrangement according to claim 30, wherein the imager is comprises one of an ultrasound imager, a computerized tomography imager, a magnet resonance imager, an x-ray imager, a fluoroscope, a positron emission tomography imager and a single photon emission computed tomography imager.

33. A patient treatment arrangement according to claim 22, wherein the fixed beam irradiation source comprises a proton source.

34. A patient treatment arrangement according to claim 22, wherein the fixed beam irradiation source comprises a source of hadrons.

35. The patient positioning apparatus of claim 1, wherein the positioner is adapted to rotate the patient support member up to 360° about at least two of the three orthogonal axes.

* * * * *